(12) United States Patent
Agarwal et al.

(10) Patent No.: US 10,772,633 B2
(45) Date of Patent: *Sep. 15, 2020

(54) METHODS AND DEVICES FOR CONNECTING NERVES

(71) Applicant: UNIVERSITY OF UTAH RESEARCH FOUNDATION, Salt Lake City, UT (US)

(72) Inventors: Jayant P. Agarwal, Salt Lake City, UT (US); Bruce Kent Gale, Taylorsville, UT (US); Himanshu Jayant Sant, Salt Lake City, UT (US); Keng-Min Lin, San Mateo, CA (US)

(73) Assignee: University of Utah Research Foundation, Salt Lake City, UT (US)

(*) Notice: Subject to any disclaimer, the term of this patent is extended or adjusted under 35 U.S.C. 154(b) by 34 days.

This patent is subject to a terminal disclaimer.

(21) Appl. No.: 15/942,965

(22) Filed: Apr. 2, 2018

(65) Prior Publication Data
US 2019/0029686 A1    Jan. 31, 2019

Related U.S. Application Data

(63) Continuation of application No. 14/352,024, filed as application No. PCT/US2012/060439 on Oct. 16, 2012, now Pat. No. 9,931,121.
(Continued)

(51) Int. Cl.
*A61B 17/11*    (2006.01)
*A61L 27/38*    (2006.01)
(Continued)

(52) U.S. Cl.
CPC ............ *A61B 17/1128* (2013.01); *A61F 2/00* (2013.01); *A61L 27/18* (2013.01); *A61L 27/3675* (2013.01);
(Continued)

(58) Field of Classification Search
CPC .. A61F 2/00; A61F 2/0063; A61F 2250/0067; A61F 13/00063;
(Continued)

(56) References Cited

U.S. PATENT DOCUMENTS

| 4,662,884 A | 5/1987 | Stensaas |
| 4,669,474 A | 6/1987 | Barrows |

(Continued)

FOREIGN PATENT DOCUMENTS

| AU | 2006329152 | 1/2012 |
| CA | 2078982 | 5/1999 |

(Continued)

OTHER PUBLICATIONS

U.S. Appl. No. 16/054,401, filed Aug. 3, 2018, Agarwal.
(Continued)

*Primary Examiner* — George J Ulsh
(74) *Attorney, Agent, or Firm* — Workman Nydegger

(57) ABSTRACT

A nerve repair conduit configured to be secured on first and second portions of a selected nerve. The nerve repair conduit includes a polymeric body having a proximal end, a distal end, an exterior surface and an interior surface defining an interior lumen. In addition, the nerve conduit includes at least one drug reservoir to hold agent(s) that may, for example, facilitate nerve regeneration. The drugs diffuse from the drug reservoir(s) into the nerve repair conduit through an outlet (e.g., a semipermeable membrane) in proximity to the first and second portions of a selected nerve. The nerve repair conduit may be configured to deliver the agent(s) at a rate having substantially zero-order kinetics and/or at a constant rate over a selected period of time (e.g., at least 1 week).

20 Claims, 5 Drawing Sheets

Related U.S. Application Data

(60) Provisional application No. 61/547,978, filed on Oct. 17, 2011, provisional application No. 61/634,362, filed on Feb. 28, 2012, provisional application No. 61/689,263, filed on Jun. 1, 2012.

(51) Int. Cl.
*A61F 2/00* (2006.01)
*A61L 27/18* (2006.01)
*A61L 27/36* (2006.01)
*A61L 27/54* (2006.01)

(52) U.S. Cl.
CPC ............. *A61L 27/383* (2013.01); *A61L 27/54* (2013.01); *A61B 2017/1132* (2013.01); *A61F 2/0063* (2013.01); *A61F 2250/0067* (2013.01); *A61L 2300/414* (2013.01); *A61L 2300/64* (2013.01); *A61L 2430/32* (2013.01)

(58) Field of Classification Search
CPC ...... A61F 13/00068; A61F 2/82; A61F 2/945; A61F 2002/821; A61F 2002/91591; A61L 27/18; A61L 27/3675; A61L 27/383; A61L 27/54; A61L 2300/414; A61L 2300/64; A61L 2430/32; A61B 17/1128; A61B 2017/1132; A61B 17/11; A61B 17/1114; A61B 2017/1107; A61B 2017/1135; A61B 2017/1139
USPC ........................................................ 606/152
See application file for complete search history.

(56) References Cited

U.S. PATENT DOCUMENTS

| | | |
|---|---|---|
| 4,759,764 A | 7/1988 | Fawcett |
| 4,774,967 A | 10/1988 | Zanakis |
| 4,778,467 A | 10/1988 | Stensaas |
| 4,870,966 A | 10/1989 | Dellon |
| 4,883,618 A | 11/1989 | Barrows |
| 4,963,146 A | 10/1990 | Li |
| 4,986,828 A | 1/1991 | de Medinaceli |
| 5,019,087 A | 5/1991 | Nichols |
| 5,354,305 A | 10/1994 | Lewis |
| 5,376,662 A | 12/1994 | Ockert |
| 5,693,085 A | 12/1997 | Buirge |
| 5,770,417 A | 6/1998 | Vacanti |
| 6,309,635 B1 | 10/2001 | Ingber |
| 6,379,382 B1 | 4/2002 | Yang |
| 6,448,076 B2 | 9/2002 | Dennis |
| 6,514,515 B1 | 2/2003 | Williams |
| 6,548,569 B1 | 4/2003 | Williams |
| 6,676,675 B2 | 1/2004 | Mallapragada |
| 6,716,225 B2 | 4/2004 | Li |
| 6,821,946 B2 | 11/2004 | Goldspink |
| 6,838,493 B2 | 1/2005 | Williams |
| 6,840,962 B1 | 1/2005 | Vacanti |
| 6,867,247 B2 | 3/2005 | Williams |
| 6,899,873 B2 | 5/2005 | Ma |
| 6,953,482 B2 | 10/2005 | Doi |
| 7,135,040 B2 | 11/2006 | Wang |
| 7,179,883 B2 | 2/2007 | Williams |
| 7,198,799 B2 | 4/2007 | Mueller |
| 7,268,205 B2 | 9/2007 | Williams |
| 7,553,923 B2 | 6/2009 | Williams |
| 7,615,063 B2 | 11/2009 | Doi |
| 7,618,653 B2 | 11/2009 | Xu |
| 7,785,628 B2 | 8/2010 | Hissink |
| 8,758,374 B2 | 6/2014 | Agarwal |
| 9,931,121 B2 | 4/2018 | Agarwal |
| 2002/0086047 A1 | 7/2002 | Mueller |
| 2002/0156150 A1 | 10/2002 | Williams |
| 2002/0173558 A1 | 11/2002 | Williams |
| 2003/0030836 A1 | 2/2003 | Maekawa |
| 2003/0072749 A1 | 4/2003 | Muir |
| 2004/0122454 A1 | 6/2004 | Wang |
| 2004/0234576 A1 | 11/2004 | Martin |
| 2005/0069525 A1 | 3/2005 | Mikael |
| 2006/0018947 A1 | 1/2006 | Mueller |
| 2007/0067883 A1 | 3/2007 | Sretavan |
| 2007/0135929 A1 | 6/2007 | Williams |
| 2007/0141166 A1 | 6/2007 | Xu |
| 2007/0182041 A1 | 8/2007 | Rizk |
| 2008/0051490 A1 | 2/2008 | Williams |
| 2008/0095823 A1 | 4/2008 | Williams |
| 2008/0132602 A1 | 6/2008 | Rizk |
| 2009/0024150 A1 | 1/2009 | Ahlers |
| 2009/0099580 A1 | 4/2009 | Priestley |
| 2009/0155326 A1 | 6/2009 | Mack et al. |
| 2010/0047310 A1 | 2/2010 | Chen |
| 2010/0055148 A1 | 3/2010 | Xu |
| 2010/0076465 A1 | 3/2010 | Wiberg |
| 2010/0094318 A1 | 4/2010 | Li |
| 2010/0168625 A1 | 7/2010 | Swain |
| 2010/0168720 A1 | 7/2010 | Swain |
| 2010/0168870 A1 | 7/2010 | Swain |
| 2010/0291180 A1 | 11/2010 | Uhrich |
| 2011/0087338 A1 | 4/2011 | Siemionow |
| 2011/0125170 A1 | 5/2011 | Hoke |
| 2011/0152898 A1 | 6/2011 | Kochevar |

FOREIGN PATENT DOCUMENTS

| | | |
|---|---|---|
| CA | 2634351 | 6/2007 |
| CA | 2713214 | 7/2009 |
| CN | 1380115 | 11/2002 |
| CN | 1843307 | 10/2006 |
| CN | 101138656 | 3/2008 |
| CN | 100479785 | 4/2009 |
| CN | 2012309013 | 5/2009 |
| CN | 101474423 | 7/2009 |
| CN | 101474424 | 7/2009 |
| CN | 101507842 | 8/2009 |
| CN | 101543645 | 9/2009 |
| CN | 101564552 | 10/2009 |
| CN | 100560037 | 11/2009 |
| CN | 101579246 | 11/2009 |
| CN | 101711893 | 5/2010 |
| EP | 261833 | 3/1988 |
| EP | 534152 | 3/1993 |
| EP | 1650224 | 4/2006 |
| EP | 1878451 | 1/2008 |
| KR | 20030087196 | 11/2003 |
| KR | 20060006295 | 1/2006 |
| KR | 100700674 | 3/2006 |
| KR | 20060018752 | 3/2006 |
| KR | 100718073 | 5/2007 |
| KR | 20090064617 | 6/2009 |
| MX | 2008006463 | 3/2009 |
| SG | 125885 | 10/2006 |
| TW | 287459 | 10/2007 |
| UA | 9421 | 9/2005 |
| WO | 1988006866 | 9/1988 |
| WO | 9005552 | 5/1990 |
| WO | 2000051622 | 11/2001 |
| WO | 2002047557 | 6/2002 |
| WO | 2000056376 | 7/2002 |
| WO | 2004101002 | 11/2004 |
| WO | 2005020825 | 3/2005 |
| WO | 2005037070 | 4/2005 |
| WO | 2007057177 | 5/2007 |
| WO | 2007071167 | 6/2007 |
| WO | 2007092417 | 8/2007 |
| WO | 2007142579 | 12/2007 |
| WO | 2008070428 | 6/2008 |
| WO | 2008/121331 | 10/2008 |
| WO | 2008140413 | 11/2008 |
| WO | 2008144514 | 11/2008 |
| WO | 2009085823 | 7/2009 |
| WO | 2009094225 | 7/2009 |
| WO | 2009117127 | 9/2009 |
| WO | 2010042207 | 4/2010 |
| WO | 2013066619 | 5/2013 |

(56) References Cited

FOREIGN PATENT DOCUMENTS

OTHER PUBLICATIONS

International Search Report and Written Opinion for PCT/US2012/060439 dated Jan. 24, 2013.
Alluin, O. et al., "Funational Recovery After Peripheral Nerve Injury and Implantaiton of a Collagen Guide" *Biomaterials*.Jan. 2009; 30(3): pp. 363-373.
Amr, S.M., et al., "Direct Cord implantation in Brachial Plexus Avulsions: Revices Technique Usign a Single Stage Combined Anterior (First) Posterior (Second) Approach and End-to-Side Side-to-Side Grafting Neurorhaphy" *J. Brachial Plex Peripher Nerve Inj.* Jun. 2009; vol. 4 Issue 8.
Amr, S.M., et al., "Repair of Brachial Plexus Lesions by End-To-Side Side-To-Side Grafting Neurorhaphy: Experience Based on 11 Cases," *Microsurgery*, 2005; 25(2) 126-46.
Arai T., et al., "Side-to-Side Neurorrhaphy in Sciatic Nerves of Rat" *Journal of Japanese Soc. Surg. Hand.* 2001, vol. 18 Issue 2, pp. 155-158.
Archibald, S.J., et al. "A Collagen-Based Nerve Guide Conduit for Peripheral Nerve Repair: an Electrophysiological Study of Nerve Regenerationin Rodents and Non-Human Primates" *Journal Comp. Neurol.* Apr. 1991; vol. 306, Issue 4, pp. 685-696.
Archibald, S.J., et al, :Factors that Influence Peripheral Nerve Regeneration: Electrophysiological Study of the Mokey Median Nerve *Ann Neurol.* 2002: vol. 51(1), pp. 69-81.
Archibald, S.J., et al, "Monkey Median Nerve Repaired by Nerve Graft or Collagen Nerve Guide Tube" *Journal of Neuroscience* 1995: vol. 15 Issue 5, pp. 4109-4123.
Bain, J.R., et al., "Functional Evaluationof Complet Sciatic, Peroneal, and Posterior Tibial Nerve Lesions in the Rat" *Plastic Reconstruction Srugery* 1989: vol. 83. pp. 129-138.
Benito-Ruiz, J., et al., "Invaginated Vein Graft as Nerve Conduit: an Experimental Study" *Microsurgery* 1994: vol. 15 Issue 2, pp. 105-115.
Berger, A., et al., "The Dellon Tube in Injuries of Peripheral Nerves" *Handchir Mikrochir Plast Chir.* Jan. 1994; vol. 26 Issue 1, pp. 44-47.
Bertleff, M.J., et al., A Prospective Clinical Evaluation of Biodegradable Neurolac Nerve Guids for Sensory Nerve Repair in the Hand *Journal of Hand Surgergons of America* May 2005; vol. 30, Issue 3; pp. 513-518.
Biers, S.M., et al., "Nerve Regeneration: Might This be the Only Solution for Functional Problems of the Urinary Tract?" *Curr Opin Urol.* Nov. 2003; vol. 13 Issue 6, pp. 495-500.
Burnett, M.G., et al., "Pathophysiology of Peripheral Nerve Injury: A Brief Review" *Nerosurg Focus.* May 2004; vol. 16 Issue 5, E1.
Chen, Z., et al., "Comparison of the Nerve Regeneration of End-to-Side Neurorrhaphy and Side-to-Side Neurorrhaphy: An Experimental Study" *Chinese Journal of Practical Hand Surgery*Jan. 2001.
Clavijo-Alverez, J.A., et al., "Comparison of Biodegradable Conduits within Aged Rat Sciatic Nerve Defects" *Plastic Reconstructive Surgery*, May 2007; vol. 119 Issue 6, pp. 1839-1851.
Cui, T., et al., "Rapid Prototyping of a Double-Layer Polyurethane-Collagen Conduit for Perpheral Nerve Regeneration" *Tissue Eng. Part C Methods.* Mar. 2009, vol. 15 Issue 1, pp. 1-9.
De Ruiter. G.C., et al., "Designing Ideal Conduits for Peripheral Nerve Repair" *Neurosurg Focus* Feb. 2009; vol. 26 Issue 2, E5.
Deumens, R., et al., "Repairing Injured Peripheral Nerves: Bridging the Gap" *Prog. Neurobiol.* Nov. 2010; vol. 92 Issue 3, pp. 245-276.
Fabre, T., et al., "Study of a (Trimethylenecarbonate-Co-Epsilon-Caprolactone) Polymer—Part 2: In Vitro Cytocompatibility Analysis and In Vivo ED1 Cell Response of a New Nerve Guide" *Biomaterials* Nov. 2001, vol. 22 Issue 22, pp. 2951-2958.
Gatta, R., "Sulla Anastomosi Latero-Terminale Dei Tronchi Nervosa" *Archivio Italiano Chirurgia.* 1938; vol. 48. pages 155-171.
Hayashi, A., et al. "Axotomy or Compression is Required for Axonal Sprouting Following End-to-Side Neurorrhaphy" *Exp. Neurol.* Jun. 2008; vol. 211 Issue 2, pp. 539-550.

Hobson, M.I., "Increased Vascularisation Enhances Axonal Regeneration within an Acellular Nerve Conduit" *Ann R. College of Surgery Engl.* Jan. 2002: vol. 84 Issue 1, pp. 47-53.
Ichihara, S., "Development of New Nerve Guide Tube for Repair of Long Nerve Defects" *Tissue Eng Part C Methods.* Sep. 2009; vol. 15 Issue 3, pp. 387-402.
Itoh, S., et al., "Evalution of Cross-Linking Procedures of Collagen Tubes Used in Peripheral Nerve Repair" *Biomaterials* Dec. 2002; vol. 23 pp. 4475-4481.
Jansen, K., et al., "Long-Term Regeneration of the Rat Sciatic Nerve Through a Biodegradable Poly (DL-Lactide-Epsilon-Caprolactone) Nerve Guide: Tissue Reactions with Focus on Collagen III/IV Reformation [Erratum]" *Journal of Biomed. Mater. Res. A.*, May 2004, vol. 69 Issue 2, pp. 334-341.
Jansen, K., et al., "A Hyaluronan-Based Nerve Guide: In Vitro Cytotoxicity, Subcutaneous Tissue Reactions, and Degradation in the Rat" *Biomaterials*, Feb. 2004, vol. 25 Issue 3, pp. 483-489.
Jeans, L.A., et al., "Peripheral Nerve Repair by Means of a Flexible Biodegradable Glass Fibre Wrap: A Comparison with Microsurgical Epineurial Repair" *Journal of Plastic Reconstruction Aesthet. Surgery*, 2007, vol. 60 Issue 12, pp. 1302-1308.
Jung, J.M., et al., "Contribution of the Proximal Nerve Stump in End-to-End Nerve Repair: In a Rat Model" *Clinical Orthopedic Surgery*, 2009, vol. 1, pp. 90-95.
Kalbermatten, D.F., et al., "New Fibrin Conduit for Peripheral Nerve Repair" *Journal of Reconstructive Microsurgery*, Jan. 2009, vol. 25 Issue 1, pp. 27-33.
Kitahara, A.K., et al., "Facial Nerve Repair Accomplished by the Interposition of a Collagen Nerve Guide" *Journal of Neurosurgery* Jul. 2000, vol. 93 Issue 1, pp. 113-120.
Kitahara, A.K., et al., "Facial Nerve Repair Using a Collagen Conduit in Cats," Scand. J. Plast. Recontr. Hand Surg. 33: 187-193, 1999.
Li, S.T., et al., "Peripheral Nerve Repair with Collagen Conduits" *Clinical Mater.* 1992, vol. 9 Issues 3-4, pp. 195-200.
Liu, B.S., "Fabrication and Evaluation of a Biodegradable Proanthocyanidin-Crosslinked Gelatin Conduit in Perihperal Nerve Repair" *Journal of Biomedical Mater. Res. A.*, Dec. 2008; vol. 87 Issue 4, pp. 1092-1102.
Ljungberg,C., et al., "Neuronal Survival Using a Resorbably Synthetic Conduit as an Alternative to Primary Nerve Repair" *Microsurgery*, 1999, vol. 19 Issue 6, pp. 259-264.
Mackinnon, S.E., "Clinical Outcome Following Nerve Allograft Transplantation" *Plastic Reconstructive Surgery*, 2001, vol. 107, pp. 1419-1429.
Mackinnon, S.E., et al., "A Primate Model for Chronic Nerve Compression" *Journal of Reconstructive Microsurgery*, 1985, vol. 1, pp. 185-194.
Sherif, M., et al., "Intrinsic Hand Muscle Reinnervation by Median-Ulnar End-to-Side Bridge Nerve Graft: Case Report" *Journal of Hand Surgery*, 2010, vol. 35A; pp. 446-450.
Matsumoto, K., et al., "Peripheral Nerve Regeneration Across an 80-mm Gap Bridged by a Polyglycolic Acid (PGA)-Collagen Tube Filled with Laminin-Coated Collagen Fibers: A Histological and Electrophysiological Evalution of Regenerated Nerves" *Brain Res.* Jun. 2000, vol. 868 Issue 2, pp. 315-328.
Meek, M.F., et al., "US Food and Drug Administration/Conformit Europe-Approved Absorbable Nerve Conduits for Clinical Repair of Peripheral and Cranial Nerves" *Ann. Plast. Surg.* Apr. 2008, vol. 60 Issue 4, pp. 466-472.
Meek, M.F., et al., "Secondary Digital Nerve Repair in the Foot with Resorbable p(DLLA-epsilon-CL) Nerve Conduits" *Journal of Reconstructive Microsurgery*, Apr. 2006, vol. 22 Issue 3, pp. 149-151.
Meyer, R.S., et al., "Functional Recovery Follwing Neurorrhaphy of the Rat Sciatic Nerve by Epineurial Repair Compared with Tubulization" *Journal of Orthopedic Research*, Sep. 1997, vol. 15 Issue 5, pp. 664-669.
Myckatyn et al., "Microsurgical Repair of Peripheral Nerves and Nerve Grafts" *Grabb and Smith's Plastic Surgery*, 6th Edition (2007).
Navarro, X., et al., "Engineering an Artificial Nerve Graft for the Repair of Severe Nerve Injuries" *Med Biol Eng Comput.* Mar. 2003, vol. 41 Issue 2, pp. 220-226.

(56) References Cited

OTHER PUBLICATIONS

Nectow, A., et al., "Biomaterials for the Development of Peripheral Nerve Guidance Conduits" *Tissue Eng Part B Review* Aug. 2011.
Okomoto, H., et al., "Recovery Process of Sciatic Nerve Defect with Novel Bioabsorbable Collagen Tubes Packed with Colagen Filaments in Dogs" *Journal of Biomedical Material Research A.*, Mar. 2010, vol. 92 Issue 3, pp. 859-868.
O'Neill, A.C., et al., "Preparation and Integration of Human Amnion Nerve Conduits Using a Light-Activated Technique" *Plastic Reconstructive Surgery*, Aug. 2009, vol. 124 Issue 2, pp. 428-437.
Papalia, I., et al., "Origin and History of End-to-Side Neurorrhaphy" *Microsurgery*, 2007, vol. 27 Issue 1, pp. 56-61.
Patel, M., et al., "GDNF-Chitosan Blended Nerve Guides: A Functional Study" *Journal of Tissue Eng Regen Med.* Sep.-Oct. 2007, vol. 1 Issue 5, pp. 360-367.
Patel, M., et al., "Collagen-Chitosan Nerve Guides for Peripheral Nerve Repair: A Histomorphometric Study" *Journal of Biomaterial Appl.* Sep. 2008, vol. 23 Issue 2, pp. 101-121.
Ray, W.Z., et al., "Management of Nerve Gaps: Autografts, Allografts, Nerve Transfers, and End-to-Side Neurorrhaphy" *Exp Neurol.* May 2010, vol. 223 Issue 1, pp. 77-85.
Smith, R.M., et al., "Role of Small Intestine Submucosa (SIS) as a Nerve Conduit: Preliminary Report" *Journal of Investigative Surgery*, Nov.-Dec. 2004; vol. 17 Issue 6, pp. 339-344.
Spyropoulou, G.A., et al., "New Pure Motor Nerve Experimental Model for the Comparative Study Between End-to-End and End-to-Side Neurorrhaphy in Free Muscle Flap Neurotization" *Journal of Reconstructive Microsurgery*, 2007, vol. 23 Issue 7, pp. 391-398.
Stevenson, T.R., et al., "Tubular Nerve Guide and Epineurial Repair: Comparison of Techniques for Neurorrhaphy" *Jouranl of Reconstructive Microsurgery*, May 1994, vol. 10 Issue 3, pp. 171-174.
Sun, M., et al., "Novel Thin-Walled Nerve Conduit with Microgrooved Surface Patterns for Enhanced Peripheral Nerve Repair" *Journal of Material Scient and Material Medicine*, Oct. 2010, vol. 21 Issue 10, pp. 2765-2774.
Taras, J.S., et al., "Repair of Lacerated Peripheral Nerves with Nerve Conduits" *Tech Hand Up Extrem Surg.* Jun. 2008, vol. 12 Issue 2, pp. 100-106.
Taras, J.S., et al., "Nerve Conduits" *Journal of Hand Therapies*, Apr.-Jun. 2005, vol. 18 Issue 2, pp. 191-197.
Teman, C.J., et al., "Quantification of Fibrosis and Osteosclerosis in Myeloproliferative Neoplasms: A Computer Assisted Image Study" *Leukemia Research*, 2010. vol. 34, pp. 871-876.
Terzis, J.K., et al., "The 'Babysitter' Procedure: Minihypoglossal to Facial Nerve Transfer and Cross-Facial Nerve Grafting" *Plastic Reconstructive Surgery*, 2009, vol. 123 Issue 3, pp. 865-876.
Tham, S.K., et al., "Motor Collateral Sprouting Throug an End-to-Side Nerve Repair" *Journal of Hand Surgery*, Sep. 1998, vol. 23 Issue 5, pp. 844-851.
Ulkur, E., et al., "Nerve Graft Prefabrication: Preliminary Study" *Journal of Reconstructive Microsurgery*, Apr. 2008, vol. 24 Issue 2, pp. 135-137.

Vasconcelos, B.C., et al., "Facial Nerve Repair with Expanded Polytetrafluoroethylene and Collagen Conduits: an Experimental Study in the Rabbit" *Journal Oral Maxillofac Surgery*, Nov. 2005, vol. 58 Issue 11, pp. 1257-1262.
Viterbo, F., et al., "End-to-Side Neurorrhaphy with Removal of Epineurial Sheath: an Experimental Study in Rats" *Plastic Reconstructive Surgery*, Dec. 1994, vol. 94 Issue 7, pp. 1038-1047.
Wangensteen, K.J., et al., "Collagen Tube Conduits in Peripheral Nerve Repair: A Retrospective Analyis" *Hand (NY)*. Nov. 24, 2009.
Watanabe, K., et al, "Nerve Conduit Using Fascia-Wrapped Fibrocollagenous Tube" *Journal of Reconstructive Microsurgery*, Jul. 2001, vol. 17 Issue 5, pp. 363-368.
Whitworth, I.H., et al., "Orientated Mats of Fabronectin as a Condit Material for Use in Peripheral Nerve Repair" *Journal of Hand Surgery Br.*, Aug. 1995, vol. 20 Issue 4, pp. 429-436.
Xiu, X.L., et al., "An Experimental Study of the Side-to-Side Neurorrhaphy to Repair Incomplete Injury of Peripheral Nerve" *The Orthopedic Journal of China* Oct. 10, 2011.
Yang, Y.C., et al., "Characteristics and Biocompatibiiity of a Biodegraable Genipin-Cross-Linked Gelating/Betatricalcium Phosphate Reinforced Nerve Guide Conduit" *Journal of Biomed Mater Res B. Appl. Biomater.*, Oct. 2010, vol. 95 Issue 1, pp. 207-217.
Yao, L., et al., "Controlling Dispersion of Axonal Regernations Using a Multichannel Collagen Nerve Conduit" *Biomaterials* Aug. 2010. vol. 31 Issue 22, pp. 5789-5797.
Yoshitatsu, S., et al., "Muscle Flap Mass Preservation by Sensory Reinnervation with Side-to-Side Neurorrhaphy: An Experimenatl Study in Rats" *Journal of Reconstructive Microsurgery*, Sep. 2008, vol. 24 Issue 7, pp. 479-487.
Yuksel, F., et al., "Nerve Regeneration Through Side-to-Side Neurorrhaphy Sites in a Rat Model: A New Concept in Peripheral Nerve Surgery" *Plastic Reconstructive Surgery*, Dec. 1999, vol. 104 Issue 7, pp. 2092-2099.
Yuksel, F., et al., "Two Applications of End-to-Side Nerve Neurorrhaphy in Severe Upper-Extremity Nerve Injuries" *Microsurgery*, 2004, vol. 24 Issue 5, pp. 363-368.
Yuksel, F., et al., "Nerve Regeneration Through a Healthy Peripheral Nerve Trunk as a Nerve Conduit: A Preliminary Study of a New Concept in Peripheral Nerve Surgery" *Microsurgery*, 2002, vol. 22 Issue 4, pp. 138-143.
Zukor, K., et al., "Regenerative Medicine: Drawing Breath After Spianl Injury" *Nature*, 2011, vol. 475, pp. 177-178.
Ho, et al., "Preservation of Muscle Viability Following Proximal Nerve Injury via Suturing a Collagen Conduit Between Damaged and Healthy Nerves," University of Utah School of Medicine & Department of Plastic and Reconstructive Surgery.
European Search Report for EP12846719 dated Apr. 7, 2015.
Lin, et al., "New Approaches to Bridge Nerve Gaps: Development of a Novel Drug-Delivering Nerve Conduit," 2012 Annual International Conference of the IEEE Engineering in Medicine and Biology Society. pp. 747-750.
U.S. Appl. No. 13/200,028, Mar. 27, 2013, Office Action.
U.S. Appl. No. 13/200,028, Feb. 12, 2014, Notice of Allowance.
U.S. Appl. No. 14/352,024, Jun. 7, 2016, Office Action.
U.S. Appl. No. 14/352,024, Jan. 13, 2017, Office Action.
U.S. Appl. No. 14/352,024, Dec. 6, 2017, Notice of Allowance.
U.S. Appl. No. 16/054,401, Mar. 6, 2020, Office Action.

METHODS AND DEVICES FOR CONNECTING NERVES

CROSS-REFERENCE TO RELATED APPLICATIONS

This application is a continuation of U.S. patent application Ser. No. 14/352,024 filed 15 Apr. 2014 and titled "METHODS AND DEVICES FOR CONNECTING NERVES," which application claims the benefit of and priority to International Application No. PCT/US12/60439, filed 16 Oct. 2012 and titled "METHODS AND DEVICES FOR CONNECTING NERVES," which claims the benefit of and priority to U.S. Prov. Pat. App. Ser. No. 61/689,263 filed 1 Jun. 2012 and titled "METHODS AND DEVICES FOR CONNECTING NERVES", U.S. Prov. Pat. App. Ser. No. 61/634,362 filed 28 Feb. 2012 and titled "METHODS AND DEVICES FOR CONNECTING NERVES," and U.S. Prov. Pat. App. Ser. No. 61/547,978 filed 17 Oct. 2011 and titled "METHODS AND DEVICES FOR CONNECTING NERVES," the entireties of which are incorporated herein by this reference.

BACKGROUND

Peripheral nerve injuries affect 2-3% of trauma patients and vastly more subsequent to tumor extirpation or iatrogenic injury. These injuries can result in chronic debilitating pain from crush or neuroma formation. Patients often suffer from life-long loss or functional disturbances mediated by the injured nerve, which can severely diminish their quality of life. Nerve injuries have a tremendous socioeconomic impact from loss of work and associated healthcare costs. Nerve lesions caused by trauma, tumor or inflammatory processes often require the removal of the injured segment of nerve and subsequent repair either by tension free end-to-end neurorrhaphy or by bridging the gap with autologous nerve grafts or nerve conduits. Inadequate or untimely repair can result in lifelong deficits in muscle function or sensation.

The current standards for repairing gaps that cannot be brought together without tension require bone shortening to allow for a tension-free repair, or the use of an autologous nerve graft. These grafts are harvested from donor sensory nerves (sural nerve or posterior interosseous nerve) and have the disadvantage of loss of sensation at the donor site as well as the need for an additional surgical site. While autologous nerve grafts serve as the state-of-the-art in repairing nerve gaps, numerous challenges associated with this approach results in functional benefits to less than about 50% of patients (e.g., only about 40-50%). These challenges include morbidity at the site of harvesting of donor nerve(s), limitations to the amount of nerve that can be harvested, mismatches in size and fascicular patterns between the nerve stumps and the graft. In recent years, grafts made from biologically derived materials have gained traction over allogenic and xenogenic tissues. Collagen, fibrin, and fibronectin have been used in addition to synthetic materials such as aliphatic polyesters and hydrogels. Much progress has been made in the field of artificial nerve conduits with collagen and polyglycolic acid conduits commercially available and in use. These hollow tubes act as axon guides for the regenerating nerves and can allow for tension free bridging without the need to harvest donor nerve.

Separately, it has been shown that locally delivering growth factors or small molecules can enhance axon sprouting and peripheral nerve recovery. In animal models, a variety of proteins or small molecules including Galectin-1, VEGF, Nerve Growth Factor ("NGF"), and Netrin-1 delivered locally can act to direct axon growth, enhance Schwann cell migration and/or enhance axon regeneration. Acellular conduits and scaffolds have limited regenerative capacity and depend on the migration of supporting cells into the local environment. Local delivery of growth factors have shown promise in recruiting nerve growth promoting cells like Schwann cells and endothelial cells and in promoting direct axon growth.

BRIEF SUMMARY

The present disclosure relates to nerve repair conduits, kits that include such conduits, and methods for using such conduits. The nerve repair conduits described herein are configured for covering a damaged portion of a nerve and deliver one or more drugs thereto increase the rate of functional recovery. For example, with a transected nerve, the nerve repair conduits described herein may secure a proximal portion of the severed nerve in proximity to a distal portion of the severed nerve. The conduits described herein may, for example, be positioned around injured (e.g., crushed), partially transected, or fully transected nerves end-to-end, end-to-side, side-to-end or side-to-side. In addition, the nerve repair conduits described herein include drug reservoirs that are positioned on the conduits inside the body (i.e., in vivo) at the site of nerve repair without the use of an external drug conduit, thus (1) continuously delivering small molecules or growth factors to the adjoined nerves at a controlled rate and (2) improving the degree of axon regeneration and functional recovery. These nerve conduits are unique in that the desired drug(s) or other agents are released from an integrated (i.e., in situ) reservoir through an outlet (e.g., a semi-permeable membrane) into the conduit lumen in proximity to the injured nerve. This delivery configuration can allow for more controlled and uniform delivery of one or more compounds rather than relying on drugs embedded in biodegradable conduits or drugs that are administered from outside the body, which may have inconsistent delivery kinetics and significant burst effects.

In one embodiment, a nerve repair conduit includes a polymeric body having a proximal end, a distal end, an exterior surface and an interior surface defining an interior lumen. The nerve repair conduit further includes one or more drug reservoirs associated with the outer surface of the polymeric body. The drug reservoirs are configured to hold a liquid or diffusible agent. Suitable examples of agents include small molecule drugs, proteins (e.g., NGF), DNA or RNA, viruses, and the like. The agent may be in liquid form, or in a suspension, a gel, a hydrogel, in a polymer matrix, or the like. In addition, the one or more drug reservoirs may be loaded with cells (e.g., Schwann cells or adipose-derived stem cells) or other bioactive agents that may aid nerve repair and recovery. In one embodiment, the one or more drug reservoirs may contain an excipient and at least one agent. The nerve repair conduit further includes at least one outlet (e.g., a semipermeable membrane) formed between the one or more drug reservoirs, the exterior surface of the polymeric body, and the interior surface of the polymeric body for delivering the at least one drug to the interior lumen of the polymeric body.

In one embodiment, the nerve repair conduit is configured to deliver at least one drug at a rate having substantially controlled kinetics (e.g., substantially zero-order or substantially first-order kinetics) over an extended period of time—e.g., at least one week, two weeks, three weeks, at least one month, or longer. In another embodiment, the nerve repair conduit may be configured to deliver at least one drug at a substantially constant rate (e.g., a selected amount of drug is delivered from the reservoir to the interior lumen per unit time) over an extended period of time—e.g., at least 24 hours, one week, two weeks, three weeks, at least one month, or longer.

In another embodiment, a method for repairing a nerve is disclosed. The method includes (1) providing a nerve repair conduit as described above, (2) securing the proximal end of the nerve repair conduit on a first portion of a nerve and securing the distal end of the nerve repair conduit on a second portion of a nerve such that the first and second portions are in fluid communication with one another via the interior lumen of the nerve repair conduit, and (3) infusing the first and second portions with at least one agent from the one or more drug reservoirs that are associated with the conduit. The first and second portions may, for example, include proximal and distal portions of an injured but still intact nerve (e.g., a crushed nerved), or the first and second portions may include proximal and distal portions of a partially or fully transected nerve. In one embodiment, the at least one agent may be delivered at a rate having substantially controlled kinetics (e.g., substantially zero-order or substantially first-order kinetics and over an extended period of time—e.g., at least one week, two weeks, three weeks, at least one month, or longer. In another embodiment, the at least one agent may be delivered at a substantially constant rate over an extended period of time—e.g., at least 24 hours, one week, two weeks, three weeks, at least one month, or longer.

In a specific embodiment, the nerve repair method described herein may include positioning a nerve graft in the nerve repair conduit, and securing the proximal end of the nerve repair conduit on the selected portion of the first nerve and securing the distal end of the nerve repair conduit on the selected portion of the second nerve such that the nerve graft acts as a bridge between the first and second nerves.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Introduction and Definitions

Figure 1A:
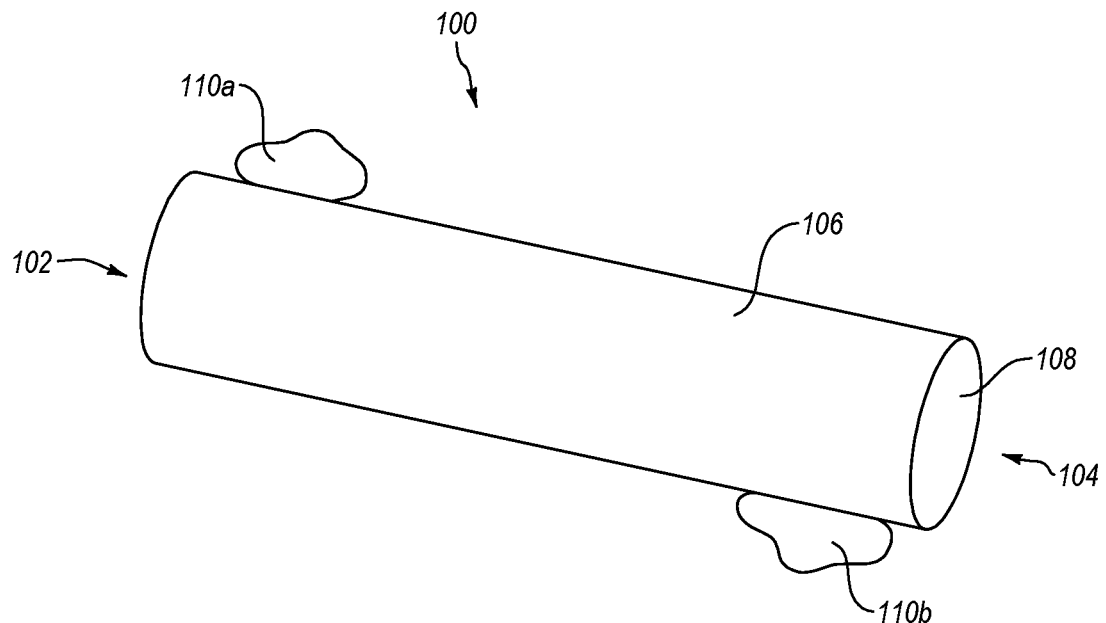
FIG. 1A illustrates a nerve repair conduit, according to one embodiment of the present invention.

The present disclosure relates to nerve repair conduits, kits that include such conduits, and methods for using such conduits. The nerve repair conduits described herein are configured for covering a damaged portion of a nerve and deliver one or more drugs thereto increase the rate of functional recovery. For example, with a transected nerve, the nerve repair conduits described herein may secure a proximal portion of the severed nerve in proximity to a distal portion of the severed nerve. The conduits described herein may, for example, be positioned around injured (e.g., crushed), partially transected, or fully transected nerves end-to-end, end-to-side, side-to-end or side-to-side. In addition, the nerve repair conduits described herein include drug reservoirs that are positioned on the conduits inside the body (i.e., in vivo) at the site of nerve repair without the use of an external drug conduit, thus (1) continuously delivering small molecules or growth factors to the adjoined nerves at a controlled rate and (2) improving the degree of axon regeneration and functional recovery. These nerve conduits are unique in that the desired drug(s) or other agents are released from an integrated (i.e., in situ) reservoir through an outlet (e.g., a semi-permeable membrane) into the conduit lumen in proximity to the injured nerve. This delivery configuration can allow for more controlled and uniform delivery of one or more compounds rather than relying on drugs embedded in biodegradable conduits or drugs that are administered from outside the body, which may have inconsistent delivery kinetics and significant burst effects.

Trauma patients with peripheral nerve injury suffer from life-long loss and/or disturbances in function mediated by the injured nerve. Nerve injuries with large gaps (>1 cm) require special bridging strategies for tension-free repair. Autologous nerve grafts (e.g., sural nerve or posterior interosseous nerve) serve as the current state-of-the-art in repairing such gaps, but numerous challenges associated with this approach results in functional benefits to only 40-50% patients. These include loss of sensation at the donor site, morbidity at the site of harvesting of donor nerve(s), limitations in the amount of nerve that can be harvested, mismatches in size and fascicular patterns between the nerve stumps and the graft, and the need for an additional surgical site. In recent years, grafts made from biologically derived materials have gained traction over allogenic and xenogenic tissues. Collagen, fibrin, and fibronectin have been used in addition to synthetic materials such as aliphatic polyesters and hydrogels. These hollow tubes act as axon guides for the regenerating nerves and can allow for tension free bridging without the need to harvest donor nerve. Separately, it has been shown that locally delivering growth factors or small molecules can enhance axon sprouting and peripheral nerve recovery. In animal models, NGF, VEGF, and GDNF delivered locally can act to direct axon growth, and/or enhance axon regeneration. Local delivery of growth factors have shown promise in recruiting nerve growth promoting cells like Schwann cells and endothelial cells and in promoting direct axon growth.

To address these issues, this disclosure relates to nerve conduits and methods for repairing injured, partially transected, or severed nerves (e.g., peripheral nerves) in a manner that facilitates healing of the of the nerve and improves patient outcomes. The nerve conduits are fabricated from a flexible, polymeric material and include a hollow annulus that serves as a guidance bridge for axons and nerve signaling molecules while a permeable outlet permits for delivery of an agent (e.g., a drug) into the annulus. The nerve repair conduits described herein are designed to continuously deliver the agent within the nerve conduit in the vicinity of the nerve repair at an essentially constant rate over an extended period of time (e.g., 1 week to 6 month) to improve the degree of nerve regeneration and functional recovery. The nerve repair conduits described herein can be used for cover injured portion(s) of nerves and/or adjoining partially transected or fully transected nerves in an end-to-end, end-to-side, side-to-end, or side-to-side fashion. The nerve conduits and the methods of their use disclosed herein have the potential to impact a broad spectrum of patients including those with nerve tumors, battlefield or other traumatic injuries and those with localized nerve inflammation.

Two components of this disclosure are: 1) nerve conduit design and 2) conduit implantation in vivo. Each of these components utilizes an innovative approach, which if successful, could fundamentally change the way peripheral nerve injuries are treated, resulting in improved outcomes and reduced disability for patients.

In one embodiment, a nerve repair conduit is disclosed. The nerve repair conduit includes a novel delivery apparatus integrated with a nerve guide conduit for delivering an agent (e.g., a drug) into the conduit. The nerve repair conduit includes a drug delivery reservoir that is attached to the nerve repair conduit. In other words, embodiments of the present disclosure may be used for nerve repair and delivery of an agent in vivo without relying on an exterior source of the source of the agent and without relying on integrating the agent directly into the material used to form the conduit.

The contents of the drug delivery reservoir (e.g., protein, small molecules, cells, nucleic acids, virus particles, etc. plus an optional excipient) are separated from the interior lumen of the conduit via an outlet (e.g., a semi-permeable membrane). The outlet is selected to allow for controlled delivery kinetics (e.g., near zero-order release kinetics or near first-order release kinetics) into the lumen of the conduit and where the agent can come into contact with and enhance growth of the regenerating nerve. In one embodiment, the device will be designed so the drug delivery reservoir does not extend all the way to the ends of the conduit. This will allow for sutures to be placed between the nerve epineurium and the conduit ends without puncturing the reservoir or membrane. This excess conduit length on either end can also be trimmed if necessary for tailored size match with the nerve gap.

Other groups have utilized hydrogels, fibrin, and polymer gels as carriers with growth factors and small molecules. These conjugated carriers were then filled into the lumen of nerve conduits as a means to locally deliver the proteins/molecules of interest. Attempts have also been made to incorporate drug into the biodegradable construct of the conduit itself. Each of these approaches has variable drug release kinetics. As the carrier or conduit construct itself biodegrades, there is often a burst of drug release that is neither sustained (i.e., not a constant rate) nor at the desired dose.

The devices and methods disclosed herein have the clear advantage of versatility of releasing a variety of different neurotrophic factors (e.g., proteins, small molecules, other neurotrophic factors, or combinations thereof) and/or other agents (e.g., cells, nucleic acids, viruses, anti-rejection drugs (e.g., steroids, cyclosporine, Prograf, etc.), or combinations thereof). That is, a variety of different drugs and/or other agents can be loaded into the drug release reservoirs of the nerve repair conduits described herein. In addition, the drug concentration, kinetics of delivery and duration of delivery can be readily adjusted by, for example, changing the size/volume of the drug release reservoirs, changing the excipient, changing the permeability or size of the outlet from the reservoirs, etc. Likewise, because the nerve repair conduits described herein can have more than one drug release reservoir, it is possible to tailor drug concentration, kinetics of delivery, duration of delivery, and/or elution rates independently. In addition, timing of release from different reservoirs can be tailored. For example, a first reservoir could be loaded with a drug that releases in the first 2 weeks and a second reservoir could be loaded with a drug that does not start to release until after 2 weeks.

For example, with the device described herein, the diffusion of each new drug can be titrated to near zero-order kinetics with iterative refinements of the outlet from the reservoirs with, for example, changes to the semi-permeable membrane pore size and surface area, reservoir size, and with the addition of a polymer matrix (e.g., polyvinyl alcohol ("PVA"), ethylene-vinyl acetate ("EVA"), hyaluronic acid, chitosan, PEG, poly-PNIPA, polyepsilon caprolactone-co-lactide-polyethylene glycol, HEMA, or a hydrogel) for controlled drug release. In one possible drug delivery scenario, the controlled release of a given drug may be driven by two separate mechanisms: (i) a semi permeable filter/membrane and (ii) a polymer matrix. This two-fold delivery mechanism can result in controlled delivery of multiple drugs and potentially tailor the release of individual drugs at different rates from the same device, thus allowing for simpler device customization. In addition, slow degradation of the matrix may prevent sudden release of drugs in the event of unlikely, but possible, unplanned leakage or puncture of the drug delivery device.

In addition to the foregoing, recent research into cell based therapies has shown promise as a means to augment peripheral nerve repair. The devices described herein have the potential to function synergistically with stem cells, Schwann cell, and epithelial cell transplants by delivering proteins or growth factors to the nerve cells to direct differentiation or stimulate function. In one example, at least one portion of the interior lumen of the devices described herein may be coated with a layer of cells that can aid the nerve repair and growth. In another example, cells may be delivered into the interior lumen from a drug reservoir.

While nerve repair is generally the focus of the present disclosure, the device described herein could be used in a variety of tissue repair and localized drug delivery strategies. For example, devices described herein have the potential for broad applicability for healing tendon and bone or local anti-tumor therapies. Likewise, the conduits described herein could be installed around injured, diseased, or repaired blood vessels to deliver agents such as anticoagulants, or VEGF to enhance blood vessel healing or possibly deliver nitric oxide at an area of blood vessel stenosis to help dilate the vessel.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein are for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings.

Although directional references, such as upper, lower, downward, upward, rearward, bottom, front, rear, etc., may be made herein in describing the drawings, these references are made relative to the drawings (as normally viewed) for convenience. These directions are not intended to be taken literally or limit the present invention in any form. In addition, terms such as "first," "second," and "third" are used herein for purposes of description and are not intended to indicate or imply relative importance or significance.

II. Nerve Repair Conduits

Referring now to FIG. 1A, one embodiment of a nerve repair conduit 100 is illustrated. The nerve repair conduit 100 includes a proximal end 102, a distal end 104, an exterior surface 106, and an interior surface 108 that defines an interior lumen. In addition, the nerve repair conduit 100 includes a first drug reservoir and a second drug reservoir schematically illustrated at 110a and 110b. The drug reservoirs 110a and 110b are attached to the outer surface 106 of the nerve repair conduit 100 such that drugs may be delivered into the interior lumen of the nerve repair conduit 100 via an outlet (e.g., a semipermeable membrane). The drug reservoirs 110a and 110b deliver drug to the interior lumen of the conduit 100 from a position inside the patient's body at the site of implantation of the nerve repair conduit 100. In other words, the drug and/or another agent is stored in and delivered from inside the body, not from a source outside the body. Likewise, the drug and/or another agent is stored in a reservoir and is not directly integrated into the polymer or another material used to form the conduit. In the embodiment illustrated in FIG. 1A, the drug reservoirs 110a and 110b may be sacs, bags, pouches, pods, bladders and the like. And while FIG. 1A illustrates two drug reservoirs 110a and 110b associated with the proximal 102 and distal 104 ends of the conduit 100, the number and positioning of the drug reservoirs may be changed without departing from the spirit of this disclosure.

Figure 1B:
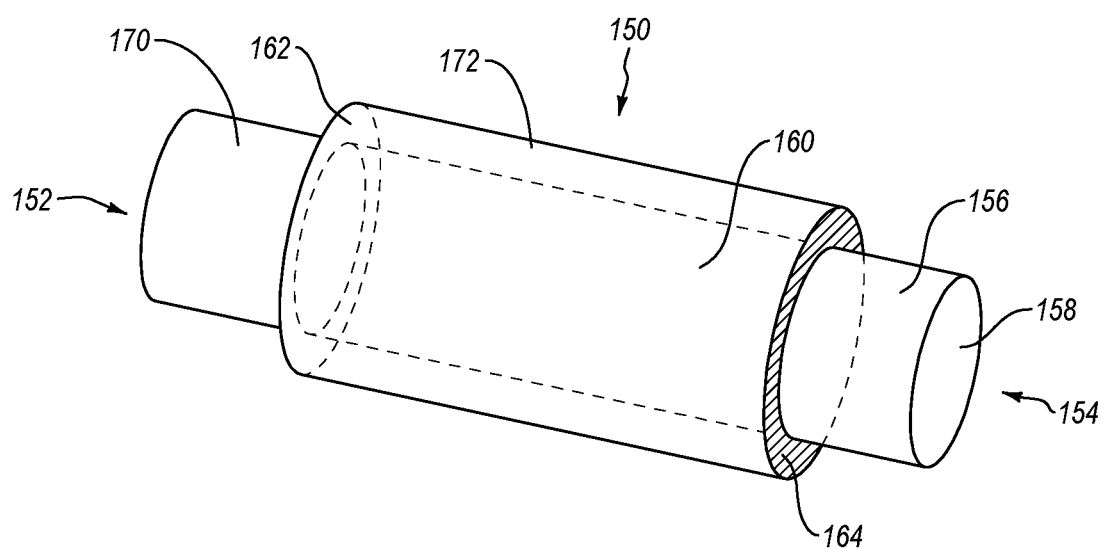
FIG. 1B illustrates a nerve repair conduit, according to one embodiment of the present invention.

Referring now to FIG. 1B, another embodiment of a nerve repair conduit 150 is illustrated. The nerve repair conduit 150 includes an inner tube 170 and an outer tube 172 that is disposed around the inner tube 170. The nerve repair conduit 150 includes a proximal end 152, a distal end 154, an exterior surface 156, and an interior surface 158 that defines an interior lumen. In addition, the nerve repair conduit 150 includes a drug reservoir 160 (i.e., the outer tube 172). The drug reservoir 160 is arranged as a concentric cylinder that surrounds at least a portion of the inner tube 170. The drug reservoir 160 is fluidly connected to the interior lumen of the inner tube 170 of the conduit 150 via an outlet (see, e.g., FIGS. 2A and 2B, elements 212a and 212b) such that drugs may be delivered into the interior lumen of the nerve repair conduit 150.

In one embodiment, the nerve repair conduit described herein may be configured to deliver the at least one drug at a substantially constant rate for at least 24 hours, one week, two weeks, three weeks, or four weeks or more (e.g., up to six months). Typically, the duration of delivery of the at least one drug is a function of one or more of a volume of the one or more reservoirs, the excipient, number of outlets, outlet size, or diffusion rate of the at least one drug through the at least one outlet. In another embodiment, the nerve repair conduit may be configured to deliver the at least one drug with, for example, substantially zero order kinetics or substantially first-order kinetics, for at least 2 weeks, three weeks, or four weeks.

As used herein, the terms "substantially zero order kinetics" or "zero order" refer to a process that has a rate that is independent of the concentration of the component(s). In diffusion, this, for example, may refer to process where the rate of diffusion of a species across a barrier (e.g., a semi-permeable membrane) is substantially independent of the concentration of the species on either side of the barrier. This may be accomplished, for example, by integrating the species into a matrix wherein the rate of diffusion is a function of the rate of release of the species from the matrix. As used herein, the terms "substantially first order kinetics" or "first order" refer to a process that has a rate that dependent on the concentration of only one component. Other components may be present, but each will be zero-order.

Figure 2A:
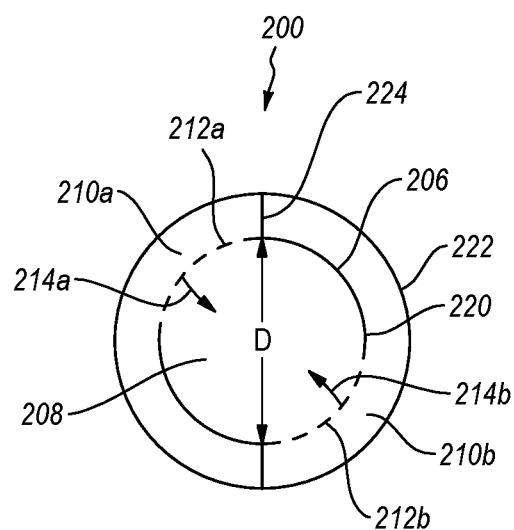
FIG. 2A illustrates an end cut-away view of the nerve repair conduit illustrated in FIG. 1B, according to one embodiment of the present invention.
Figure 2B:
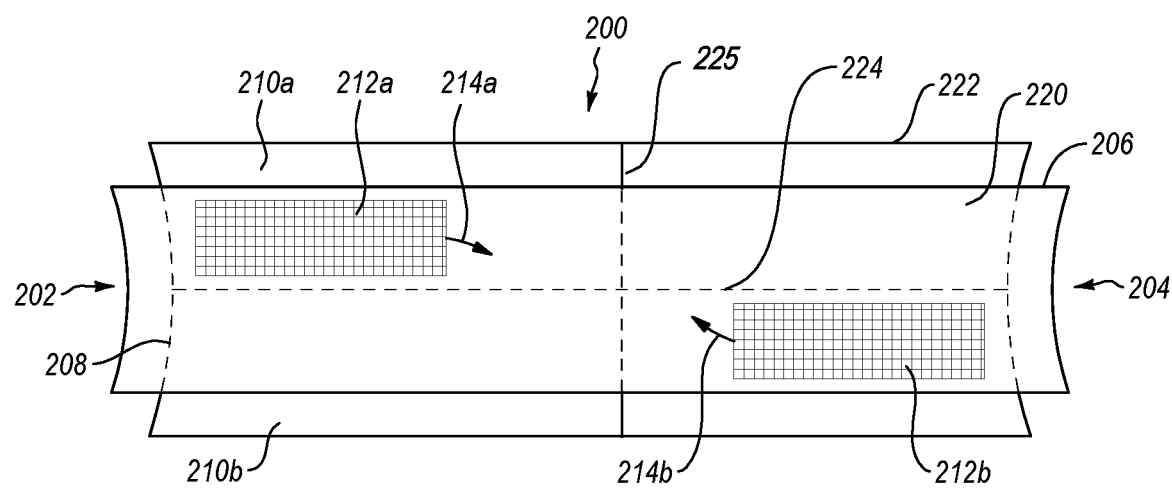
FIG. 2B illustrates a side cut-away view of the nerve repair conduit illustrated in FIG. 1B, according to one embodiment of the present invention.

Referring now to FIGS. 2A and 2B, an end cut-away view and a side cut-away view of a nerve repair conduit 200 are illustrated. The nerve repair conduit 200 is similar to the embodiment of FIG. 1B except that they outer tube 222 is divided by a divider 224 that extends between the inner tube 220 and the outer tube 222 such that the outer tube 222 and the inner tube define a first reservoir 210a and a second reservoir 210b. While the divider 224 is shown as dividing the reservoir horizontally (i.e., oriented along the long axis of the nerve repair conduit 200), divider(s) (such as divider 225) may also be oriented orthogonal to the long axis of the nerve repair conduit 200 such that different reservoirs are positioned in different longitudinal sections of the nerve repair conduit 200. In another embodiment (not shown), reservoirs 210a and 210b may be further divided to form additional drug reservoirs. Outlets 212a and 212b are formed in the inner tube 220 forming a passageway between the drug reservoirs 210a and 210b, the exterior surface 206 of the conduit 200, and the interior surface 208 of the conduit 200. The outlets 212a and 212b allow for drug to diffuse from the drug reservoirs 210a and 210b into the interior lumen of the conduit 200. The diffusing drug is illustrated by arrows 214a and 214b.

As shown in FIG. 2B, it appears that outlets 212a and 212b are formed on or affixed to the inner surface 208 of the conduit 200. However, one will appreciate that the outlets 212a and 212b may be affixed to or formed on surface 206, or outlets 212a and 212b may be integrally formed on either surface 206 or 208. In one embodiment, the outlets 212a and 212b may be formed by affixing a semi-permeable membrane to the inner 208 or outer 206 surface of the conduit 200. The outlets 212a and 212b are configured to allow drug to diffuse from the drug reservoirs to the interior lumen of the conduit. In one embodiment, an outlet may have a nominal pore size of 1 nm, 2 nm, 3 nm, 4 nm, 5 nm, 6 nm, 7 nm, 8 nm, 9 nm, 10 nm, or larger depending in the application and the size of the drug that needs to diffuse through the outlet. Suitable examples of a semipermeable membranes having such pore sizes include, but are not limited to, polyether sulfone ("PES"), ethylene-vinyl acetate ("EVA"), PLGA, and other semipermeable membranes known on the art. In another embodiment, the outlets one 212a and 212b may be formed by forming holes (e.g., by laser cutting) that extend between the outer 206 and inner 208 surfaces. In addition to forming holes in the inner tube 222, the inner surface 208 may be etched (e.g., laser etching), scratched, or formed with longitudinal grooves that may act as guides for regenerating axons. The holes may be nano-scale holes, micro-scale holes, otherwise sized, or combinations thereof.

The nerve repair conduit 200 may have an interior D diameter of about 0.5 mm to about 2 cm, about 1 mm to about 1 cm, about 1 mm to about 5 mm, about 2 mm to about 4 mm, or about 2.5 mm to about 3 mm. For example, for repairing a typical peripheral nerve, a repair conduit having an inner diameter of about 1-2 mm may be sufficient. However, for repairing a major nerve (e.g., the sciatic nerve) and conduit having a size of 1-2 cm may be necessary.

The nerve repair conduits described herein (e.g., conduits 100, 150, and 200) may be fabricated from a polymeric material. In one embodiment, the polymeric material may be a flexible polymeric material. The nerve repair conduits described herein may be fabricated from biodegradable and/or non-biodegradable materials. Suitable examples of materials that can be used to fabricate the nerve repair conduits described herein include, but are not limited to, poly(lactic-co-glycolic acid) ("PLGA"), collagen, spun silk, electrospun silk, polytetrafluoroethylene ("PTFE"), poly-dimethylsiloxane ("PDMS"), silicone, a salicylic acid-based polymer, a salicylsalicylic acid-based polymer, a difluoro-phenyl-salicylic acid-based polymer, collagen, fibrin, fibronectin, alginate, gelatin, keratin, thrombin, poly-gly-colic acid, poly-(lactic acid), poly-caprolactone, poly-(L-lactic acid), poly(3-hydroxybutyric acid), poly((bis(hy-droxyethyl) terephthalate-ethyl phosphoester/terephthaloyl chloride), poly(2-hydroxyethyl methacrylate) ("PHEMA"), a co-polymer of PHEMA and methyl methacrylate, poly (acrylonitrile-co-methylacrylate), and combinations thereof.

The nerve conduits described herein may be fabricated by a number of techniques. For example, the conduits described herein may be cast, injection molded, or micromachined (e.g., by xurography or laser). In one example, the inner tube 220 of the conduit 200 may be fabricated by dissolving the polymer (e.g., PLGA) in a compatible solvent (e.g., acetone) and then casting the inner tube 220 in a glass capillary tube. As the solvent evaporates, the polymer clings to the walls of the capillary and an interior lumen is formed by evaporation of the solvent. Once the solvent has evaporated, the annular inner tube 220 may be recovered by breaking the glass mold. The outlet(s) may be formed by cutting one or more holes (i.e., windows) in the inner tube 220 and affixing a semi-permeable membrane over the hole. For example, the semi-permeable membrane may be affixed to the inner tube with glue. In another embodiment, the outlet(s) may be formed by laser cutting holes in the inner tube. The holes may include nano-scale holes, micro-scale holes, other holes, or combinations thereof. In another example, the outlet(s) may be formed by biodegradation of the inner tube 220 of the conduit 200. In yet another example, the outlet(s) may be formed by adjusting the polymer makeup of the material used to form the inner tube such that the drug(s) can diffuse directly through the wall of the inner tube into the interior lumen of the conduit.

The outer tube 222 (i.e., the drug reservoir tube) may be fabricated in a similar fashion, except a a larger capillary tube may be used to obtain the larger diameter of the outer tube 222. The reservoir 210 may formed be by arranging the outer tube 222 around the inner tube 220 and sealing the open ends of the outer tube 222. The open ends of the outer tube may be sealed with, for example, glue or plugs. Once formed, the reservoir may be filled by injecting drug(s) and an optional excipient (e.g., PVA) into the reservoir with, for example, a hypodermic needle. The hole formed in the reservoir may be sealed with a drop of glue or polymer (e.g., PLGA).

Suitable examples of agents that may be used in the reservoir(s) include, but are not limited to, neurotrophic factors, pain medications (e.g., opioids), antirejection drugs (e.g., glucocorticoids), antimicrobials, nerve stimulating drugs (e.g., agrin), NSAIDs, small molecule drugs (e.g., epoxy eicosanoids), nucleic acids (e.g., DNA or RNA), viruses carrying nucleic acids for transfection of cells in around the nerve. and the like. In addition, the reservoir(s) may be loaded with cells (e.g., Schwann cells or adipose derived stem cells), and cells that release growth factors or cytokines, or combinations thereof. Suitable examples of neurotrophic factors include one or more of nerve growth factor ("NGF"), glial cell-derived neurotrophic factor ("GDNF"), vascular endothelial growth factor ("VEGF"), netrtin-1, or fibroblast growth factor ("FGF").

In one embodiment, where multiple reservoirs are filled with different agents, the separate agents may have at least one of different release rates, different durations of release, different release times, or different release locations in the interior lumen. For example, different release rates, different release times, and different release locations in the interior lumen may be accomplished by using different semipermeable membranes, different membrane areas, different excipients, and/or different outlet locations.

In addition to infusing the interior lumen with drug agents, the inner surface 208 of the conduit 200 may be coated with cells that may aid nerve healing or repair. In one embodiment, the interior lumen of the conduit 200 may be lined with one or more of Schwann cells, stem cells or blast cells (e.g., adipose derived stem cells, mesenchymal stem cells, bone marrow derived stem cells, neural tube lineage cells, etc.), or epithelial cells. Cells such as Schwann cells, stem cells, and blast cells may, for example, provide molecular factors that aid nerve healing and repair while epithelial cells may, for example, help with revascularization of the tissue surrounding the repair site.

Figure 3A:
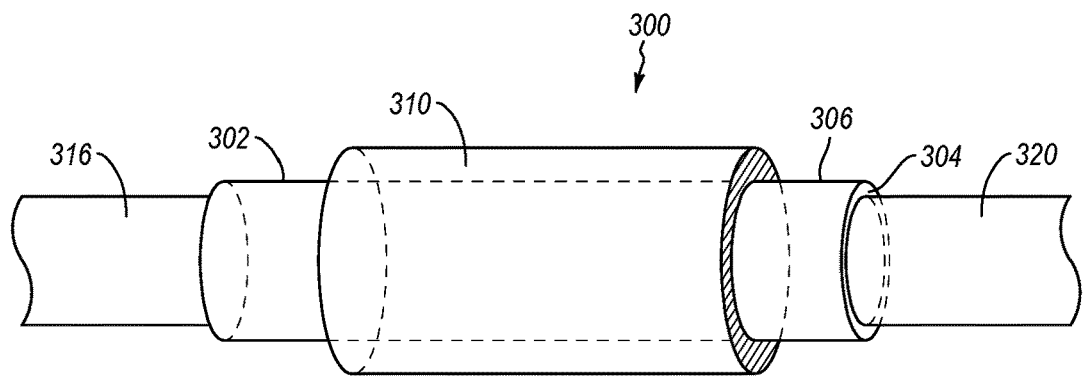
FIG. 3A illustrates a side elevation view of a nerve repair conduit adjoining a transected nerve in an end-to-end fashion, according to one embodiment of the present invention.
Figure 3B:
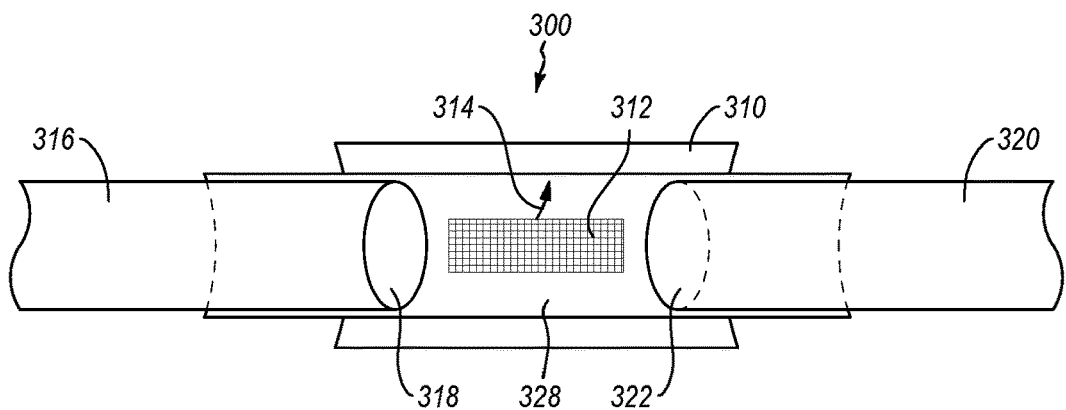
FIG. 3B illustrates a partial cut-away view of a nerve repair conduit adjoining a transected nerve in an end-to-end fashion, according to one embodiment of the present invention.

Referring now to FIGS. 3A and 3B, a side elevation view of a nerve repair conduit adjoining a transected nerve in an end-to-end fashion and a partial cut-away view of a nerve repair conduit adjoining the transected nerve are shown. The nerve includes a proximal end 316 and a distal end 320. The nerve repair conduit 300 includes a proximal end 302, a distal end 304, an exterior surface 306, an interior surface 308 that defines an interior lumen, and a drug reservoir 310. A drug outlet 312 is shown on the interior surface 308 of the conduit 300. The proximal end 318 and the distal end 322 of the nerve are placed into proximity to one another in the interior lumen. Diffusion of the drug out of the outlet 312 into proximity of the proximal end 318 and the distal end 322 of the nerve is shown at 314.

Figure 3C:
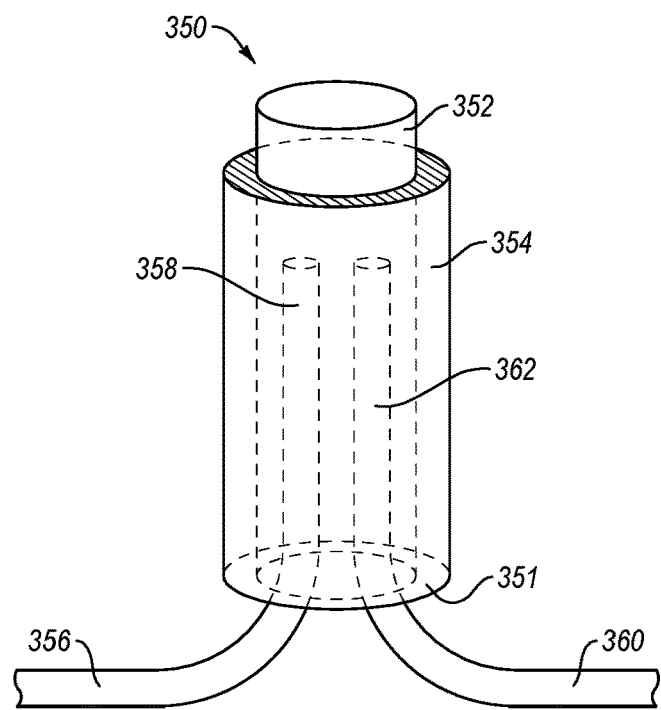
FIG. 3C schematically illustrates a partial cut-away view of a nerve repair conduit adjoining a transected nerve in a side-to-side fashion, according to one embodiment of the present invention.

Referring now to FIG. 3C, a partial cut-away view of a nerve repair conduit 350 adjoining a transected nerve in a side-to-side fashion is schematically illustrated. The principle of operation of the nerve repair conduit 350 is similar to the nerve repair conduit 300 described in FIGS. 3A and 3B. The nerve repair conduit 350 includes an open proximal end 351, a closed distal end 352, and a drug reservoir 354. The nerve includes a first portion 356 and a second portion 360. The nerve ends 358 and 362 are adjoined in the conduit and may be secured to one another by one or more sutures (not shown). The nerve repair conduit 350 may be secured to either or both of the nerve ends 358 and 362 with one or more sutures (not shown). As in the previous examples, the drug reservoir 354 may be loaded with one or more agents that can be delivered into the vicinity of the nerve ends 358 and 362 to speed/improve healing, improve patient outcomes, and the like. Additional discussion of side-to-side nerve repair can be found in U.S. patent application Ser. No. 13/200,028, the entirety of which is incorporated herein by reference.

Figure 4:
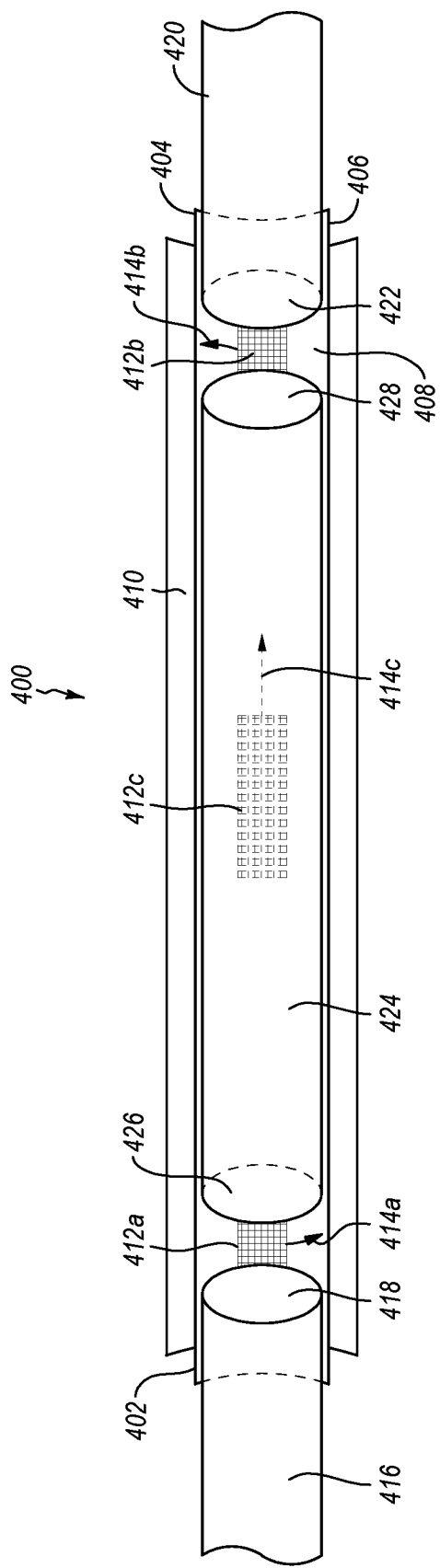
FIG. 4 illustrates a partial cut-away view of a nerve repair conduit that includes a nerve graft adjoining a transected nerve with the nerve graft positioned between the nerve ends, according to one embodiment of the present invention.

Referring now to FIG. 4, a partial cut-away view of an alternate embodiment of a nerve repair conduit 400 that includes a nerve graft 424 for adjoining a transected is illustrated. Typically, the nerve conduits shown in FIGS. 3A and 3B are only able to repair nerves with a gap of about 2-3 cm. For injured nerves with larger gaps (e.g., larger than about 2-3 cm), a nerve graft can serve as a bridge. The nerve repair conduit 400 includes a proximal end 402, a distal end 404, an exterior surface 406, an interior surface 408 that defines an interior lumen, and a drug reservoir 410. The nerve repair conduit 400 includes a number of drug outlets 412a, 412b, and 412c.

The nerve conduit 400 includes a nerve graft 424. The transected nerve includes a proximal end 416 and a distal end 420. The nerve conduit 400 includes a nerve graft 424. The first end of the nerve 418 and the second end of the nerve 422 and bridged by the nerve graft. In one embodiment, the nerve graft 424 may be an autograft harvested from the patient. In another embodiment, the nerve graft 424 may be an allograft. For example, an allograft may be harvested from a cadaver. Where the graft 424 is an allograft, xenograft, or a decellularized graft, the reservoir 410 may, for example, include at least one anti-rejection drug selected to prevent rejection of the graft.

III. Methods of Nerve Repair

In one embodiment, a method for repairing a nerve is disclosed. The method includes (1) providing a nerve repair conduit as described above, (2) securing the proximal end of the nerve repair conduit on a first portion of a nerve and securing the distal end of the nerve repair conduit on a second portion of a nerve such that the first and second portions are in fluid communication with one another via the interior lumen of the nerve repair conduit, and (3) infusing the first and second portions with at least one agent from the one or more drug reservoirs that are associated with the conduit. The first and second portions may, for example, include proximal and distal portions of an injured but still intact nerve (e.g., a crushed nerved), or the first and second portions may include proximal and distal portions of a partially or fully transected nerve.

In one embodiment, the at least one agent may be delivered at a rate having substantially controlled kinetics (e.g., substantially zero-order or substantially first-order kinetics and over an extended period of time—e.g., at least one week, two weeks, three weeks, at least one month, or longer. In another embodiment, the at least one agent may be delivered at a substantially constant rate over an extended period of time—e.g., at least 24 hours, one week, two weeks, three weeks, at least one month, or longer.

In one embodiment, the first and second nerves may be connected end-to-end. In another embodiment the first and second nerves may be connected side-to-side. Also end-to-side, side-to-end The first and second nerves may include proximal and distal segments of a transected or partially transected peripheral motor or sensory nerve.

In a specific embodiment, the nerve repair method described herein may include positioning a nerve graft in the nerve repair conduit and securing the proximal end of the nerve repair conduit on the selected portion of the first nerve and securing the distal end of the nerve repair conduit on the selected portion of the second nerve such that the nerve graft acts as a bridge between the first and second nerves.

In one embodiment, the nerve graft may be an allograft. If an allograft, xenograft, or a decellularized graft is used, the method may further include infusing the nerve graft with at least one anti-rejection drug from the one or more drug reservoirs in order to prevent rejection of the graft.

IV. Examples

Example 1

PLGA-BSA Release/Leakage Test

A 7-day release/leakage test was performed in order to explore the capacity of the PLGA device to deliver drugs of interest. Bovine serum albumin (BSA) was chosen to serve as the drug because its size is bigger than most of the growth factors. Two samples filled with 30 µL 300 mg/mL BSA were tested with two negative controls, two leakage test samples and a positive control, as shown in Table 1.

TABLE 1

List of samples involved in the PLGA-BSA release/leakage test

| Sample Name | Purpose | Reservoir | Protein in the Reservoir | Receiver chamber |
|---|---|---|---|---|
| Positive Control (PC) est. conc. 1800 ug/mL | The maximum possible conc. in the receiver chamber. | n/a | 42 uL 300 mg/mL BSA directly injected into the | 7.5 mL PBS (tween free) *Note: use |

TABLE 1-continued

List of samples involved in the PLGA-BSA release/leakage test

| Sample Name | Purpose | Reservoir | Protein in the Reservoir | Receiver chamber |
|---|---|---|---|---|
| | Use design's dimension: max 42 uL drug reservoir volume. | | PBS | 7 mL Amber Glass Vial |
| Leakage Test 1 (LT1) | To test if no BSA is detected when using a device filled with BSA and without window & filter. | #1 | 30 uL 300 mg/ml BSA | 7.5 mL PBS |
| Leakage Test 1 (LT2) (duplicate LT1) | Duplicate LT1 | #2 | 30 uL 300 mg/ml BSA | 7.5 mL PBS |
| Negative Control 1 (NC1) | To test the device without BSA and with filter & window will show no BSA in the receiver chamber. | #3 | 30 uL PBS | 7.5 mL PBS |
| Negative Control 2 (NC2) (duplicate NC1) | Duplicate NC1 | #4 | 30 uL PBS | 7.5 mL PBS |
| Sample 1 | Sample of interest. with device, with window, with BSA | #5 | 30 uL 300 mg/mL BSA | 7.5 mL PBS |
| Sample 2 | Another sample. Exactly the same as Sample 1. | #6 | 30 uL 300 mg/mL BSA | 7.5 mL PBS |

Figure 5:
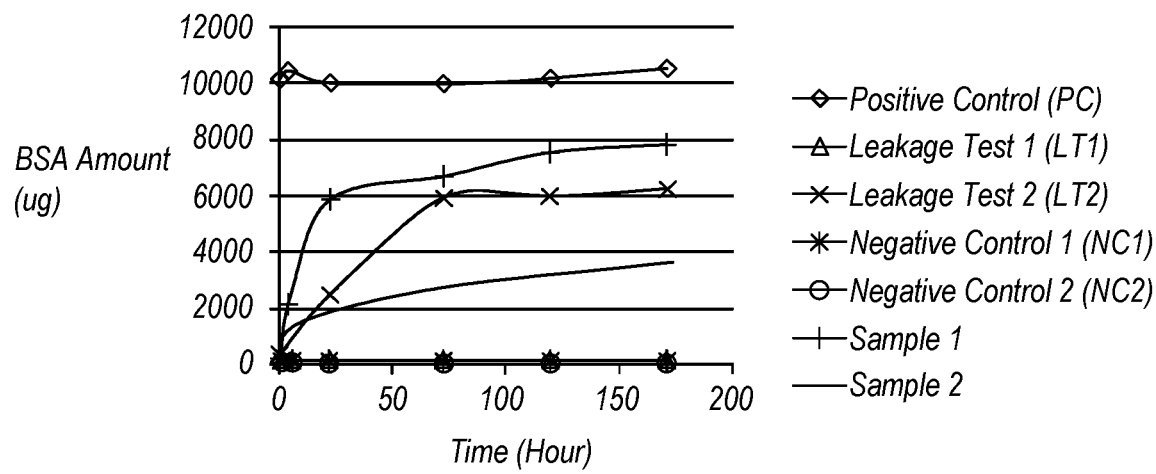
FIG. 5 is a graph illustrating the cumulative amount of bovine serum albumin ("BSA") released in a simulated drug release/leakage test with a nerve repair conduit as described herein.
Figure 6:
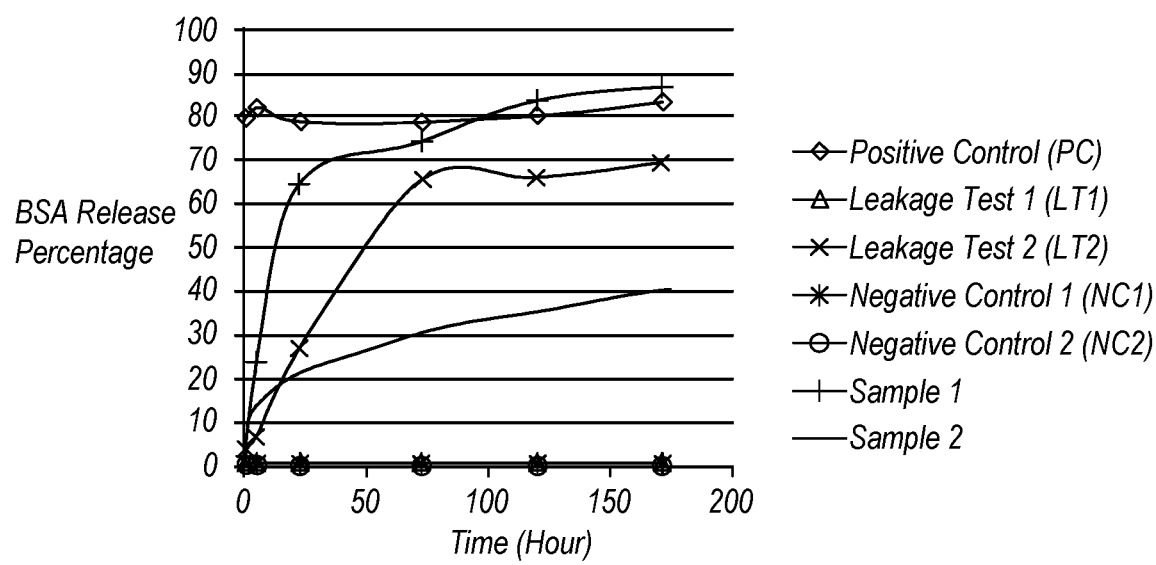
FIG. 6 is a graph illustrating the percentage of BSA released versus time in the simulated drug release/leakage test with a nerve repair conduit as described herein.

BSA concentrations in the receiver chamber of each vial were obtained from the calibration equation generated from the plate reader. Cumulative BSA release into the receiver chamber and the percentage release of BSA in the receiver chamber were plotted based on the BSA concentration values. FIGS. 5 and 6 show the result in micrograms and percent, respectively.

For the leakage test, one of the two samples (LT1 and LT2) leaked through the side of the PLGA outer tube when filling BSA into the reservoir, and therefore LT2 shows a signal raising in both FIGS. 5 and 6. On the other hand, LT1 shows no leakage and no noticeable BSA release was detected in the receiver chamber.

For the release test, Sample 1 has a rapid release (64.8%) in the first 24 hours, and slowed down in the next 6-day period. Sample 2, on the other hand, released BSA promptly in the first 4 hours (13.7%) and showed a constant release rate for the rest of the time.

For future application, growth factors that can promote axon growth may be filled into the drug reservoir with polyvinyl alcohol (PVA) to control the release kinetics, if slower release rate is preferred.

Example 2

Long-Term Placement of PLGA Repair Conduits

PLGA conduits with drug reservoirs were used to repair transected nerves in an end-to-end and a side-to-side fashion in a mouse sciatic nerve model in order to determine whether biodegradation of PLGA causes an adverse reaction. Walking track analysis was performed every two weeks until animals were sacrificed at day 90. It was found that long-term placement of PLGA conduits and biodegradation of PLGA produced no adverse reaction. In general, side-to-side repair seemed to show some advantages, but side-to-side repair is not always an option if there is a nerve gap. However, it is expected that all repair outcomes (e.g., side-to-side, end-to-end, side-to-end, etc.) can be improved with the drug-delivering conduits described herein.

Example 3

Long-Term Animal Testing

The drug delivery conduits described herein will be tested in a mouse sciatic nerve model. NGF and GDNF are two of many growth factors implicated in improved peripheral nerve regeneration and will be the test drugs for these experiments as they have been shown to enhance nerve growth both in vitro and in vivo. The mouse sciatic nerve has been established as a viable model for evaluation of peripheral nerve injury because of its easy accessibility and reasonable size for testing. It is hypothesized that the novel strategy described herein will provide results superior to nerve conduit alone (without drug) and will approach the results of autologous nerve graft. The device will also be used in combination with an autologous nerve graft and it is hypothesized that this combination will provide superior results to autologous nerve graft alone.

Experimental design: This efficacy study will utilize a mouse sciatic nerve gap (10 mm) model using transgenic mice that express GFP (green fluorescent protein) only in their peripheral nerves (Jackson Laboratories). The following groups will be included: Group 1 (n=16): sham transection; Group 2 (n=16): transection with no repair of the 10 mm gap; Group 3 (n=16): transection followed by interposition with an autologous nerve graft; Group 4 (n=16): transection followed by interposition with an empty PLGA conduit; Group 5 (n=16): transection followed by interposition with a PLGA conduit and NGF; Group 6 (n=16): transection followed by interposition with a PLGA conduit and GDNF; Group 7 (n=16): transection followed by interposition with a PLGA conduit along with NFG and GDNF; Group 8 (n=16): transection followed by interposition with autologous nerve graft surrounded with PLGA nerve guide and NGF; Group 9 (n=16): transection followed by interposition with autologous nerve graft surrounded with PLGA nerve guide and GDNF; Group 10 (n=16): transection followed by interposition with autologous nerve graft surrounded with PLGA nerve guide and NGF and GDNF. NGF and GDNF loading dosages will be based on optimal concentrations from Aim 2.

Surgery: Prior to surgery the mice will be anesthetized using isoflurane. The surgical area will be shaved and prepared with betadine. A longitudinal incision will then be made in the posterior distal thigh of the hind limb, separating the natural plane between the vertebral head of the biceps femoris and superior gluteal muscles. Under the operating microscope, a 1 cm segment of the sciatic nerve will be isolated. For Groups 2-10 the sciatic nerve will be transected to produce a 10 mm gap. For Groups 3 and 8-10 (autologous), the nerve segment removed during the transection will then be reversed and reattached with epineural sutures in an end-to-end fashion. For the other groups the same sciatic nerve gap will be created but the gap will be bridged with a conduit. For Groups 8-10, the device will be slid onto the transected nerve end and the nerve graft will then be sutured in place. Once the graft is in place, the device will be slid over the graft and the two repair sites and secured with sutures from epineurium to the device. It should be noted that the reservoir will not extend all the way to the edge of the conduit. There will be a cuff of conduit on each end of the device, which will serve as sites where sutures can be placed to anchor the device. Half of the animals in each group (n=8/group) will be sacrificed at 30 days and the other half at 90 days. The walking track, conduit, motor endplate, retrograde labeling, and gastrocnemius muscle atrophy will all be evaluated at 30 and 90 days.

Walking Track: Preoperatively and every two weeks after surgery a functional assessment of the animals' gait will be performed. Briefly, the mouse's hind feet are pressed on an inkpad before walking along an 8×52 cm track. The sciatic, tibial, and peroneal functional indices are then calculated based on paw print measurements. These indices provide a gross estimate of major muscle group functional status.

Conduit Evaluation: The conduit will initially be evaluated for the volume of NGF and GDNF remaining in the reservoir, the presence of any leaks, and the amount of each drug in the surrounding tissue and serum using commercially available ELISAs. The sciatic nerve inclusive of the conduit will then be harvested, fixed in formalin, embedded in paraffin, and sectioned. Fluorescent microscopy will be used to assess nerve growth into the conduit, since the transgenic mouse nerves express GFP. Slides will also be stained with H&E, S-100, PGP 9.5 and CD31. The different stains and fluorescent imaging will be used to assess axon growth (number, diameter, and density), Schwann cell density, and blood vessel density within the conduit. Additionally, the conduit will be evaluated for degree of degradation and the surrounding tissue evaluated for reaction to the presence of the conduit.

Motor Endplate Evaluation: The tibialis anterior muscle will be stained en bloc with alpha-bungarotixin conjugated to Alexa 594 (Molecular Probes, OR) to label the acetylcholine receptors, DAPI to identify nuclei, and the nerves themselves already express GFP. The whole mounts will be imaged using confocal microscopy by merging and flattening a stack of images taken 5 µM apart. Multiple images will be evaluated for the percentage of re-innervated neuromuscular junctions.

Retrograde Labeling: The gastrocnemius of the anesthetized animals will be injected with Fast Blue (Polysciences, Warrington, PN) six days prior to necropsy. At necropsy, the animal will be perfused and the spinal cord at L2-L4 will be harvested, placed in cold cryoprotective media, frozen in OTC compound, and sectioned (20-30 µM). The sections will be examined by fluorescent microscopy to determine labeled motor neuron density.

Gastrocnemius Muscle: The gastrocnemius of both legs will be harvested at necropsy being careful to dissect at the tendinous origin and insertion. The muscles will be weighed and the degree of atrophy of the experimental leg calculated both in terms of absolute (grams) and relative atrophy [(experimental-control)/control*100)]. Additionally, the nuclear density of the gastrocnemius will be obtained on H&E stained slides.

Electrophysiology: Sciatic nerve and muscle function will be examined immediately prior to animals' sacrifice at 90 days. These studies will only be performed on the 90 day groups. To assay motor function, the sciatic nerve proximal to the nerve transection will be stimulated, and record evoked muscle compound action potentials (mCAPs) in the plantar flexor (e.g., gastrocnemius) and dorsiflexors (e.g., tibialis anterior) muscles, and possibly nerve compound action potentials (nCAPs) distal to the transection (e.g., on tibial and peroneal branches). To assay sensory function, nCAPs proximal to the transection evoked by distal sensory stimulation will be recorded. Metrics will include size and conduction velocity of CAPs on the transected and contralateral side, and will be compared across experimental groups.

Anticipated results: It is anticipated that better outcomes will be observed, as determined by greater improvements to sciatic functional behavioral and physiological indexes, greater nerve in-growth into the conduit, and less gastrocnemius atrophy in the groups that are treated with our novel conduit-drug delivery device with NGF and/or GDNF compared to control groups. It is anticipated that the combined autologous nerve and drug-filled conduit group will show the best results. This may provide insight into a novel paradigm for treating peripheral nerve gaps with both autologous nerve and drug delivery as a means to further improve outcomes.

Potential pitfalls and alternative approaches: Drug release may differ in vivo from in vitro kinetics. If it is found that too rapid or too slow elution is occurring in vivo, that knowledge can be used to re-engineer pore size and surface area of the semi-permeable membrane on the drug delivery device. Inadvertent mechanical insult to the device may cause a leak. It is not anticipated that a significant untoward effect with a leak of such a small volume of drug; nevertheless, any observed leak will call for troubleshooting for future prevention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:
1. A nerve repair conduit configured to be implanted in vivo, the nerve repair conduit comprising:
   a polymeric body having a proximal end, a distal end, an exterior surface and an interior surface, the interior surface defining an interior lumen of the polymeric body, wherein the polymeric body is configured to be secured to a first portion of a nerve and a second portion of a nerve;

a plurality of drug reservoirs positioned adjacent to the exterior surface of the polymeric body each configured to enable delivery of an agent from the reservoir through the exterior surface;

at least one outlet formed between each of the drug reservoirs, the exterior surface of the polymeric body, and the interior surface of the polymeric body so as to enable delivery of the agent to the interior lumen of the polymeric body without requiring degradation of the polymeric body for release of the agent; and one or more dividers defining separate drug reservoirs.

2. The nerve repair conduit of claim 1, wherein the one or more dividers are oriented orthogonal to a long axis of the nerve repair conduit.

3. The nerve repair conduit of claim 1, wherein the one or more dividers are oriented along a long axis of the nerve repair conduit.

4. The nerve repair conduit of claim 1, wherein each outlet is configured to deliver its agent at a rate having substantially zero-order kinetics and over a period of time of at least 1 week.

5. The nerve repair conduit of claim 1, wherein the separate reservoirs provide at least one of different agent release rates or different agent release times.

6. The nerve repair conduit of claim 1, wherein at least one of the agents includes a neurotrophic factor selected to enhance the rate of nerve regeneration.

7. The nerve repair conduit of claim 6, wherein the neurotrophic factor includes one or more of nerve growth factor ("NGF"), glial cell-derived neurotrophic factor ("GDNF"), vascular endothelial growth factor ("VEGF"), netrin-1, or fibroblast growth factor ("FGF").

8. The nerve repair conduit of claim 1, further comprising a nerve graft positioned within the interior lumen.

9. The nerve repair conduit of claim 8, wherein at least one of the agents includes an anti-rejection drug.

10. The nerve repair conduit of claim 1, wherein the interior lumen is lined with one or more of Schwann cells, stem cells, blast cells, cells secreting growth factors or related neurotrophic factors, or epithelial cells.

11. The nerve repair conduit of claim 1, wherein the polymeric body is comprised of one or more of poly(lactic-co-glycolic acid) ("PLGA"), silk, polytetrafluoroethylene ("PTFE"), polydimethylsiloxane ("PDMS"), silicone, a salicylic acid-based polymer, a salicylsalicylic acid-based polymer, a difluorophenyl-salicylic acid-based polymer, collagen, fibrin, fibronectin, alginate, gelatin, keratin, thrombin, poly-glycolic acid, poly-(lactic acid), poly-caprolactone, poly-(L-lactic acid), poly(3-hydroxybutyric acid), poly((bis(hydroxyethyl) terephthalate-ethyl phosphoester/terephthaloyl chloride), poly(2-hydroxyethyl methacrylate) ("PHEMA"), a co-polymer of PHEMA and methyl methacrylate, or poly(acrylonitrile-co-methylacrylate).

12. The nerve repair conduit of claim 1, wherein the polymeric body has an interior diameter in a range of about 0.5 mm to about 2 cm.

13. The nerve repair conduit of claim 1, wherein each of the outlets includes one or more of a semi-permeable membrane, nano-scale holes, or micro-scale holes.

14. The nerve repair conduit of claim 13, wherein the semi-permeable membrane comprises one of polyethersulfone ("PES") ethylene-vinyl acetate ("EVA"), or PLGA.

15. The nerve repair conduit of claim 1, wherein at least one of the agents comprises an excipient including one or more of polyvinyl alcohol ("PVA"), EVA, hyaluronic acid, chitosan, PEG, poly-PNIPA, polyepsilon caprolactone-co-lactide-polyethylene glycol, HEMA, or a hydrogel.

16. A method of repairing a nerve, the method comprising:

providing a nerve repair conduit as in claim 1;

securing the proximal end of the polymeric body to the first portion of the nerve and the distal end of the polymeric body to the second portion of the nerve such that the first and second portions of the nerve are each positioned within the lumen of the polymeric body; and allowing the separate drug reservoirs to deliver their respective agents to the first and second nerve portions.

17. The method of claim 16, wherein the nerve is a crushed nerve, or wherein the first and second nerve portions are opposite ends of a transected nerve.

18. The method of claim 17, wherein the first and second portions of the nerve are positioned end-to-end, end-to-side, side-to-end or side-to-side.

19. A nerve repair device configured for in vivo implantation at a nerve repair site, the nerve repair device comprising:

an inner tube configured to receive a first portion of a nerve and a second portion of a nerve;

a drug reservoir formed as an outer tube concentrically surrounding the inner tube, the drug reservoir being configured to hold one or more agents; and an outlet disposed between the drug reservoir and the inner tube, the outlet comprising one or more of a semi-permeable membrane, nano-scale holes, or micro-scale holes, wherein the outlet is configured to allow sustained delivery of the one or more agents from the drug reservoir into a lumen of the inner tube at a substantially zero-order kinetic rate and without requiring degradation of the inner tube or drug reservoir for release of the one or more agents.

20. The nerve repair conduit of claim 19, further comprising a divider to divide the drug reservoir into a plurality of separate sections.

* * * * *